United States Patent [19]

Jones

[11] Patent Number: 4,542,221

[45] Date of Patent: Sep. 17, 1985

[54] EXCHANGING FLUORINE FOR CHLORINE IN A CHLORINATED PYRIDINE WITH AN ALKALI METAL FLUORIDE

[75] Inventor: Edward M. Jones, Kings Lynn, England

[73] Assignee: The Dow Chemical Company, Midland, Mich.

[21] Appl. No.: 500,686

[22] Filed: Jun. 3, 1983

Related U.S. Application Data

[63] Continuation of Ser. No. 264,490, May 18, 1981, abandoned.

[51] Int. Cl.$^4$ .......................................... C07D 213/02
[52] U.S. Cl. .................................... 546/345; 546/304; 546/297
[58] Field of Search ......................................... 546/345

[56] References Cited

PUBLICATIONS

Chambers et al., Journal of the Chemical Society, London, pp. 594–597 (1965).
Chemical Abstracts, vol. 68, No. 5, Abstract No. 21,504m, Jan. 29, 1968, abstracting German Pat. No. 1,248,024, issued Aug. 24, 1967.

*Primary Examiner*—Alan L. Rotman
*Attorney, Agent, or Firm*—S. Preston Jones; Ronald G. Brookens

[57] ABSTRACT

A process for preparing a fluoropyridine compound by reacting a chlorinated pyridine compound with a molar excess of an alkali metal fluoride, especially potassium fluoride, in the presence of a catalytic amount of a catalyst selected from halides of organometals and halides of metals of the iron, nickel and copper groups, and which is preferably $FeCl_3$, whereby at least one chlorine atom of the chlorinated pyridine compound is replaced by a fluorine atom. Of special interest is the preparation of 3,5-dichloro-2,4,6-trichloropyridine from pentachloropyridine.

The compounds prepared by such a process are useful for the preparation of agriculturally-useful fluoropyridines.

11 Claims, No Drawings

EXCHANGING FLUORINE FOR CHLORINE IN A CHLORINATED PYRIDINE WITH AN ALKALI METAL FLUORIDE

This is a continuation of application Ser. No. 264,490 filed May 18, 1981 now abandoned.

BACKGROUND OF THE INVENTION

The present invention is directed to a process for preparing fluorinated pyridines from chlorinated pyridines. In the present process an improved fluorination reaction between a chlorinated pyridine compound and an alkali metal fluoride is set forth. Products of the reaction are useful as intermediates for the preparation of herbicides or pesticides.

British Patent Specification No. 1,256,082 teaches the reaction of chloropyridines with potassium fluoride in a polar aprotic solvent and in the presence of a small amount of water to effect replacement of chlorine by fluorine. Reaction of pentachloropyridine with anhydrous KF in a 1:5.9 mole ratio in sulpholane and water at 215° C. has given 91% yield of 3,5-dichlorotrifluoropyridine, 6% yield of 3-chlorotetrafluoropyridine, and 3% yield of 3,4,5,6-tetrachlorofluoropyridine.

Reaction of pentachloropyridine with KF in a 1:11 mole ratio of 400° C. for 18 hours in the absence of a solvent has given 84% yield of 3,5-dichloro-2,4,6-trifluoropyridine (J. Chem. Soc. 1964, 3573). Reaction of pentachloropyridine with KF in a 1:9.5 mole ratio at 400° C. for 5 hours in the absence of solvent has given 45% yield of 3,5-dichlorotrifluoropyridine and 19% yield of 3-chlorotetrafluoropyridine (J. Chem. Soc. 1965, 594).

SUMMARY OF THE INVENTION

The present invention is directed to a process for preparing fluorinated pyridines by the fluorination of a chlorinated pyridine with an alkali metal fluoride in the presence of a catalyst.

It has now been found that certain compounds are effective catalysts for the reaction and that carrying out the reaction in the presence of a small amount of one or more of these compounds permits use of less alkali metal fluoride and lower temperatures than heretofore for preparing a given desired product in good yield.

Accordingly, the present invention provides a process for preparing a fluoropyridine compound, which process comprises reacting a chlorinated pyridine compound with from 1.0 to 1.33 moles of an alkali metal fluoride, for each chlorine atom to be replaced, in the presence of a catalytic amount of a catalyst selected from halides of organometals and halides of metals of the iron, nickel and copper groups, whereby at least one chlorine atom of the chlorinated pyridine compound is replaced by fluorine. The desired product may be isolated from the reaction mixture by distillation.

The starting material may be any pyridine compound containing at least one chlorine substituent on the ring. The useful starting materials include, for example, the mono-, di-, tri-, tetra- and pentachloropyridines, depending on the particular product or products desired. When the starting material is a polychloropyridine, the number of chlorine atoms replaced by fluorine is believed to be dependent on the temperature and time of reaction employed, the higher temperatures and longer times of reaction favoring more replacement of chlorine atoms by fluorine. The process of the invention is of special interest for the preparation of 3,5-dichloro-2,4,6-trifluoropyridine from pentachloropyridine; 3,5-dichloro-2,6-difluoropyridine from 2,3,5,6-tetrachloropyridine and 2,6-difluoropyridine from 2,6-dichloropyridine.

The alkali metal fluoride used in the process of the present invention may be cesium, potassium or sodium fluoride. The use of potassium fluoride at preferred.

An essential feature of the present process is the utilization of a catalyst selected from those listed above, such as, for example, a bromide for chloride of aluminium, antimony, or iron. Preferred catalysts include $SbCl_3$, $AlCl_3$, $ZnCl_2$ and $FeCl_3$, with the latter being most preferred. In order to obtain the benefits of the present invention, it is also essential that the catalyst be employed in an amount sufficient to provide a catalytic effect. Having regard to economy and ease of carrying out the reaction, the catalyst is generally employed in an amount of from 0.5 to 10, preferably from 1 to 5, more preferably from 1 to 3, percent by weight based on the amount of the alkali metal fluoride.

For economic reasons, it is generally preferred to carry out the reaction of the process of this invention without the use of a solvent, although the reaction can be run in the presence of a solvent or reaction medium, such as sulpholane.

It is preferred to carry out the reaction in equipment in which the parts contacted by the reactants are constructed of materials which are inert to alkali metal fluorides, such as stainless steel, nickel or Hastelloy C.

The conditions under which the reaction is carried out are such that the reactants are in their liquid or gaseous states. Below 150° C. there is a tendency for the reactants to be in their solid states, and accordingly it is preferred to carry out the reaction at a temperature within the range of from 150° to 400° C., preferably at a temperature within the range of from 250° to 350° C. and more preferably at a temperature of from 270° to 320° C. The reaction is preferably carried out, with agitation, in sealed vessels necessitating elevated pressures which are dependent on the temperatures used and the number of moles of starting material. Typically the pressure is in the range of from 10 to 350 psig and preferably from 200 to 300 psig.

A particularly preferred process of the present invention comprises reacting with agitation, in a sealed inert vessel pentachloropyridine with from 1.0 to 1.33 moles of potassium fluoride per chlorine atom of the pentachloropyridine to be replaced by fluorine in the presence of from 1 to 3 percent by weight of $FeCl_3$ based on the amount of potassium fluoride and in the absence of a solvent at a temperature within the range of from 270° to 320° C., and recovering 3,5-dichloro-2,4,6-trifluoropyridine as the principal product.

The fluoropyridine compounds prepared according to the present invention are particularly useful as intermediates for the preparation of agriculturally-useful fluoropyridine compounds. Examples of such agriculturally-useful fluoropyridine compounds which can be prepared employing the fluoropyridine compounds prepared as taught herein include compounds as follows:

(a) Compounds of general formula:

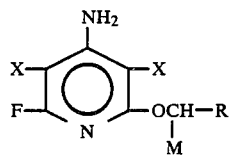

wherein each X independently represents chloro, bromo or fluoro; R represents —CONR$^2$R$^3$ (where R$^2$ and R$^3$ independently each represents hydrogen or alkyl containing from 1 to 8 carbon atoms), —COOH or a salt thereof, or —COOR$^4$ (where R$^4$ represents alkyl containing from 1 to 12 carbon atoms or —(CH$_2$)$_n$OR$^5$ where n represents an integer of from 2 to 4 and R$^5$ represents lower alkyl or phenyl); and M represents hydrogen or lower alkyl.

Such compounds, agriculturally-useful compositions containing them, and their uses are described and claimed in British Patent Specification No. 1,418,979.

(b) A compound of formula:

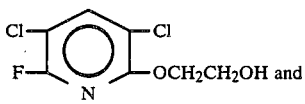

(c) A compound of formula:

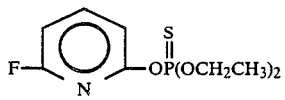

Any agriculturally-useful fluoropyridine, including those specified in (a) to (c) above, which has been prepared directly or indirectly from a fluoropyridine prepared by a process according to the present invention is within the scope of the present invention. So is an agriculturally-useful composition comprising any such agriculturally-useful fluoropyridine. Those compounds specified in (a) and (b) above are herbicidally active and the compound specified in (c) above is a nematocide.

The agriculturally-useful fluoropyridines can be prepared from the fluoropyridines prepared by the process of the present invention by any appropriate route. A typical example of one such route is as follows:

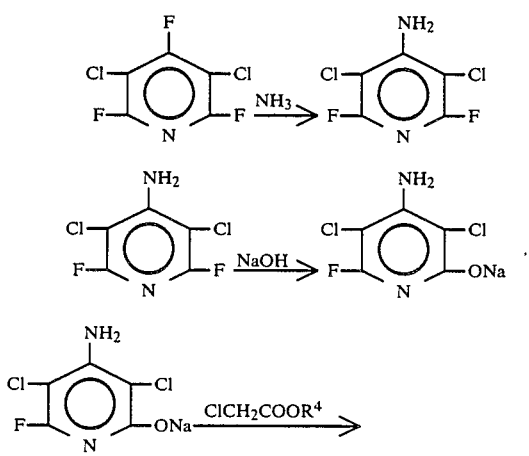

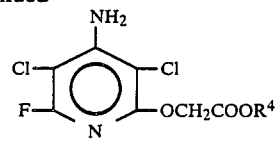

where R$^4$ is as defined above.

It will be apparent to those skilled in the art that a wide range of agriculturally-useful fluoropyridine can be prepared from a fluoropyridine which has been prepared by the process according to the present invention.

In order that the present invention may be more fully understood, the following Examples are given primarily by way of illustration and should not be construed as limitations upon the overall scope of the present invention.

EXAMPLE 1

A mixture of 232.4 g potassium fluoride and 2.3 g ferric chloride was prepared by grinding together the two components. In like manner, 251.3 g (1.0 mole) of pentachloropyridine were mixed with 236.9 g (4.0 moles KF) of the KF/FeCl$_3$ mixture. The mixing operations were carried out in a dry nitrogen atmosphere. The mixture of the reactants was placed in a 1 liter capacity stainless steel "Parr bomb" and the bomb sealed. Then the bomb and contents were heated, with agitation, at 300° C. for 5 hours with a pressure of 260 psig generated. After cooling, the contents were extracted with dichloromethane and filtered. Analysis by gas chromatography indicated an 88.7 percent yield of 3,5-dichloro-2,4,6-trifluoropyridine and a 0.6 percent yield of 3-chloro-2,4,5,6-tetrafluoropyridine.

EXAMPLE 2

The method for this Example was similar to Example 1 except as follows. The reaction mixture contained 251.3 g (1.0 mole) pentachloropyridine and 236.9 g (4.0 mole KF) of the KF/FeCl$_3$ mixture, and the reaction temperature was 350° C. and the pressure was 340 psig. There was obtained, 4.3 percent yield of a mixture of 2,4-difluoro-3,5,6-trichloropyridine and 2,6-difluoro-3,4,5-trichloropyridine and 54.2 percent yield of 3,5-dichloro-2,4,6-trifluoropyridine and a 24.9 percent yield of 3-chloro-2,4,5,6-tetrafluoropyridine.

EXAMPLE 3

Example 2 was repeated except that the temperature was 225° C. and the pressure was 10 psig. There was obtained a 21.4 percent yield unreacted pentachloropyridine. 32.6 percent yield of the 2- and 4-fluoro-tetrachloropyridine isomers, 27.6 percent yield of a mixture of 2,4-difluoro-3,5,6-trichloropyridine and 2,6-difluoro-3,4,5-trichloropyridine and a 17.2 percent yield of 3,5-dichloro-2,4,6-trifluoropyridine.

I claim:

1. A process for preparing 3-chloro-2,4,5,6-tetrafluoropyridine, 3,5-dichloro-2,4,6-trifluoropyridine, 2,4-difluoro-3,5,6-trichloropyridine, or 2,6-difluoro-3,4,5-trichloropyridine from pentachloropyridine, 3,5-dichloro-2,6-difluoropyridine from 2,3,5,6-tetrachloropyridine, or 2,6-difluoropyridine from 2,6-dichloropyridine, which process comprises reacting the polychloropyridine with from 1.0 to 1.33 moles of an alkali metal fluoride per chlorine atom to be replaced, at a temperature within the range of from 150° to 400° C.

with agitation and in the presence of a catalytic amount of a metal chloride compound selected from the group consisting of $SbCl_3$, $AlCl_3$, $ZnCl_2$ and $FeCl_3$.

2. A process as defined in claim 1, wherein the catalyst is employed in an amount of from 0.1 to 10 percent by weight based on the amount of alkali metal fluoride.

3. A process as defined in claim 1, wherein the alkali metal fluoride employed is KF.

4. A process as defined in claim 1, wherein the rection is carried out in the absence of a solvent.

5. A process as defined in claim 1, wherein the reaction is carried out at a temperature within the range of from 250° to 350° C.

6. A process as defined in claim 5 wherein the reaction is carried out at a temperaure within the range of from 270° to 320° C.

7. A process as defined in claim 1, wherein the chlorinated pyridine compound reactant is pentachloropyridine.

8. A process as defined in claim 7, wherein the principal product is 3,5-dichloro-2,4,6-trifluoropyridine.

9. A process for preparing a fluoropyridine compound, which process comprises reacting in a sealed inert vessel, with agitation, pentachloropyridine with from 1.0–1.33 moles of potassium fluoride per chlorine atom of the pentachloropyridine to be replaced by fluorine in the presence of from 1 to 3 percent by weight of $FeCl_3$ based on the amount of potassium fluoride and in the absence of a solvent at a temperature within the range of from 270° to 320° C., and recovering 3,5-dichloro-2,4,6-trifluoropyridine as the principal product.

10. A process as defined in claim 1 wherein the reaction is carried out in a sealed, inert vessel under autogenous pressure.

11. A process as defined in claim 1 wherein the catalyst employed is $FeCl_3$.

* * * * *